(12) United States Patent
Lee et al.

(10) Patent No.: US 9,028,506 B2
(45) Date of Patent: May 12, 2015

(54) AMNION INSERTION DEVICE

(76) Inventors: Keun Young Lee, Seoul (KR); Keun Ho Lee, Bucheon-Si (KR)

( * ) Notice: Subject to any disclaimer, the term of this patent is extended or adjusted under 35 U.S.C. 154(b) by 238 days.

(21) Appl. No.: 13/261,155

(22) PCT Filed: Jan. 24, 2011

(86) PCT No.: PCT/KR2011/000489
§ 371 (c)(1),
(2), (4) Date: Jan. 27, 2012

(87) PCT Pub. No.: WO2011/122760
PCT Pub. Date: Oct. 6, 2011

(65) Prior Publication Data
US 2012/0130394 A1 May 24, 2012

(30) Foreign Application Priority Data

Mar. 31, 2010 (KR) .......................... 10-2010-0029211

(51) Int. Cl.
*A61B 17/42* (2006.01)
(52) U.S. Cl.
CPC .......... *A61B 17/42* (2013.01); *A61B 2017/4225* (2013.01)
(58) Field of Classification Search
USPC .............. 604/515, 96.01, 514, 523, 915, 604/103.07–103.09, 103.14, 101.01, 604/101.02, 104–107, 118, 164.03, 164.02, 604/101.05, 97.01, 97.02, 102.01–102.03, 604/103, 912; 606/213, 153, 119, 193, 125, 606/194, 127, 128, 200, 110–115, 192, 606/198; 530/850, 851

See application file for complete search history.

(56) References Cited

U.S. PATENT DOCUMENTS

| | | | |
|---|---|---|---|
| 5,624,399 A * | 4/1997 | Ackerman | 604/103.03 |
| 5,868,779 A * | 2/1999 | Ruiz | 606/194 |
| 6,264,633 B1 * | 7/2001 | Knorig | 604/102.01 |
| 6,344,045 B1 * | 2/2002 | Lim et al. | 606/108 |
| 2002/0183777 A1 * | 12/2002 | Shannon | 606/192 |
| 2003/0023204 A1 * | 1/2003 | Vo et al. | 604/103.07 |
| 2003/0163114 A1 * | 8/2003 | Gershowitz | 604/509 |
| 2005/0167032 A1 * | 8/2005 | Lumauig | 156/158 |
| 2005/0267409 A1 * | 12/2005 | Shkolnik | 604/103.06 |
| 2007/0255209 A1 * | 11/2007 | Crooms et al. | 604/104 |

* cited by examiner

*Primary Examiner* — Jocelin Tanner
(74) *Attorney, Agent, or Firm* — MAXON IP, LLC; Justin H. Kim

(57) ABSTRACT

An amnion insertion device has been developed for an emergency cervical cerclarge operation to push back the bulged amnion into the uterus. The present invention is configured with a dilation balloon that forms at the front end portion of the air injection tube for stably supporting a support. Once the dilation balloon is inflated the inflated state will prevent deflation or sliding backwards during the cervical cerclarge operation while the bulged amnion is being pushed back into the uterus to facilitate the operation. Because the external tube and air injection tube have integrally formed a dual-tube configuration, a surgeon on duty can entirely grip the amnion insertion device by one hand, and will have the other hand free to stitch up the cervix.

6 Claims, 3 Drawing Sheets

⇐ FLUID INFLOW

AMNION INSERTION DEVICE

CROSS-REFERENCE TO RELATED APPLICATION(S)

This application claims the benefit of Korean Patent Application No. 2010-0029211, filed on Mar. 31, 2010 in the Korean Intellectual Property Office, the disclosure of which is incorporated herein by reference.

BACKGROUND OF THE INVENTION

1. Field of the Invention

Embodiments of the present invention relate to an amnion insertion device to push a bulged amnion back into a uterine cavity during an urgent cervical cerclage operation. More particularly, embodiments of the present invention relate to an amnion insertion device by which a bulged amnion is pushed back into the uterine cavity without damaging the bulged amnion using a dilation balloon inflated by air applied through an air injection tube fitted in an external tube while being integrated with the external tube and an air communication hole, and then a cervix is stitched up, to treat cervical incompetence, and in which the dilation balloon formed at a front end portion of the air injection tube is not deformed or pushed backwards when pushing the bulged amnion back into the uterine cavity, to facilitate an urgent cervical cerclage operation, and in which the external tube and air injection tube are integrated with each other, so that the amnion insertion device may be entirely gripped by one hand of an operator, leaving the other hand available to be used for stitching up the cervix, thereby maximizing efficiency of the cervical cerclage operation.

2. Related Prior Art

As well known, cervical incompetence is a medical condition in which a pregnant woman's cervix begins to efface due to a functional or structural defect of the cervix without pain or bleeding before the fetus has reached term. Thus, cervical incompetence may cause the amnion to bulge out of the uterine cavity, resulting in miscarriage or preterm birth during the second and third trimesters. Occurrence rate of cervical incompetence is 0.1% to 2% for all pregnant women. 15% of all preterm births occurring at 16 to 28 weeks gestational age are due to cervical incompetence. Thus, cervical incompetence is closely related to a morbidity or death rate of new born babies.

Medical treatment for cervical incompetence includes preventive cervical cerclage operation or urgent cervical cerclage operation carried out when a length of the cervix is observed to be short in an ultrasonic detection.

Although the cervix effaces, this may not be noticed of or diagnosed. Thus, an appropriate preventive cerclage operation or urgent cerclage operation may not be executed in time. In this case, the amnion bulges out of the uterine cavity and a delivery inevitably occurs.

In the case of cervical incompetence where the cervix effaces and the amnion bulges out of the uterine cavity, the urgent cerclage operation may be executed as the best approach. In the urgent cerclage operation, the bulged amnion is pushed back into a uterine cavity and then the cervix is stitched up.

Conventional methods for pushing the bulged amnion back into the uterine cavity include a trendelenburg position method, a method of injecting a saline solution into a bladder and a method of inserting the amnion into the uterine cavity using a sponge forcep or foley catheter.

In the trendelenburg position method, the amnion naturally moves back into the uterine cavity by lifting up feet while the patient lies on her back. In the method of injecting a saline solution into a bladder, a given amount of the saline solution is injected into the bladder so that the amnion is pushed back up by the injected saline solution. In the method using the sponge forcep, an operator pinches wet gauze using the sponge forcep and directly pushes the amnion back into the uterine cavity.

Among such cervical cerclage methods, the method using the sponge forcep has mainly been used. In this method, the amnion may be damaged due to sharpness of the gauze. The amnion may be again bulged out of the uterine cavity particularly when drawing the wet gauze out of the uterine cavity after pushing the amnion into the uterine cavity.

The conventional method using the foley catheter may be valid when the cervix opens to a small extent. However, when the amnion bulges out of the uterine cavity, it is difficult to push the amnion back into the uterine cavity because the foley catheter may be bendable.

Recently, to solve such problems, Korean Patent No. 710905 discloses an amnion insertion device including, as shown in FIG. 1, an air injection tube 10 to inject air through operation of an air injection means 12 formed at a rear end of the air injection tube 10, a dilation balloon 30 formed at a front end of the air injection tube 10 to be inflated by air injected through the air injection tube 10 and thus to directly push a bulged amnion back into a uterine cavity; a guide pipe 40 to receive the air injection tube 10 at other region than a dilation balloon 30 formation region and to allow the amnion to be easily inserted into the uterine cavity by preventing the air injection tube 10 from bending; an air hole 50 formed at one side of the air injection tube on which the dilation balloon 30 is formed, to communicate air injected through the air injection tube 10 to the dilation balloon 30. Especially, the dilation balloon 30 is characterized in that the dilation balloon 30 is fixed to the guide pipe 40 using an adhesive material in order that the dilation balloon 30 coming into an inflated state is prevented from moving left or right by a force generated when pushing the bulged amnion back into the uterine cavity.

In the amnion insertion device disclosed in Korean Patent No. 710905, the dilation balloon 30, as shown in FIG. 2, is configured be attached to an outer surface of a front end portion of the air injection tube 10. Accordingly, although the dilation balloon 30 is fixed to the guide pipe 40 at a rear end portion of the dilation balloon 30, the dilation balloon 30 may move left or right or be pushed backwards for a structural reason thereof during pushing the bulged amnion back into the uterine cavity. Thus, it is difficult to insert the bulged amnion back into the uterine cavity.

In the amnion device disclosed in Korean Patent No. 710905, the air injection tube 10 serving as an air channel to inject air into the dilation balloon 30, and the guide pipe 40 connected to an outer surface of the air injection tube 10 are not integrated with each other but are formed as individual components. Therefore, during a cervical cerclage process, a single operator should operate the amnion insertion device to push the bulged amnion back into the uterine cavity while gripping the guide pipe 40 of the amnion insertion device using one hand and gripping the air injection tube 10 using the other hand. Thus, in case when carrying out the cervical cerclage operation using the amnion insertion device disclosed in Korean Patent No. 710905, two operators may be necessary to operate the amnion insertion device and carry out the cervical cerclage operation respectively. As a result, this may cause waste of labor and further lead to an unexpected operation result in particular when the two operators do not effectively cooperate.

Moreover, in the amnion insertion device disclosed in Korean Patent No. 710905, there may occur a limitation as to dilation extent of the dilation balloon 30 because thickness of the dilation balloon 30 is very small and further the dilation balloon 30 moves left or right or is pushed backwards when pushing the bulged amnion back into the uterine cavity. In a certain case, the amnion excessively bulges out of the uterine cavity and hence the amnion may be damaged if the amnion is forcibly pushed back. In this case, in order to prevent the amnion from being damaged during the cervical cerclage process, amniocentesis should be carried out in advance to discharge some of amniotic fluid from the amnion and hence reduce the size of the amnion. After amniocentesis, the bulged amnion may be pushed back into the uterine cavity using the amnion insertion device. That is, before the cervical cerclage operation, the size of the amnion must be reduced.

SUMMARY OF THE INVENTION

Therefore, it is one aspect of the present invention to provide an amnion insertion device which may be used in an urgent cervical cerclage operation to treat cervical incompetence in which a pregnant woman's cervix effaces and thus an amnion bulges out of the uterine cavity, by which a bulged amnion is pushed back into the uterine cavity without damaging the bulged amnion using a dilation balloon inflated by air supplied through an air injection tube fitted in an external tube while being integrated with the external tube and an air communication hole, and then a cervix is stitched up, to treat cervical incompetence, and in which the dilation balloon formed at a front end portion of the air injection tube is not deformed or pushed backwards when pushing the bulged amnion back into the uterine cavity, to facilitate the urgent cervical cerclage operation, and in which the external tube and air injection tube are integrated with each other, so that the amnion insertion device may be entirely gripped by one hand of an operator, leaving the other hand free to stitch up the cervix, thereby maximizing efficiency of the cervical cerclage operation.

It is another aspect of the invention to provide an amnion insertion device used in an urgent cervical cerclage operation, which, when the amnion excessively bulges out of the uterine cavity, may effectively insert the amnion into the uterine cavity by appropriately adjusting a dilation extent of the dilation balloon in accordance with bulging of the amnion, eliminating the need to carry out the amniocentesis to discharge some of the amniotic fluid from the amnion in order to reduce the size of the amnion.

Additional aspects of the invention will be set forth in part in the description which follows and, in part, will be obvious from the description, or may be learned by practice of the invention.

In accordance with one aspect of the present invention, an amnion insertion device may include an air injection tube to inject fluid through an operation of an air injection means formed at one end of the air injection tube; a dilation balloon formed at the other end of the air injection tube to be inflated by fluid injected through the air injection tube so as to directly push a bulged amnion back into the uterine cavity; an external tube to receive the air injection tube in an integrated manner with the air injection tube at other region than a dilation balloon formation region; and a support coupled between the external tube and dilation balloon.

In accordance with one embodiment of the present invention, the air injection tube may inject a predetermined amount of fluid through an operation of the air injection means formed at one end thereof. The injected predetermined amount of fluid may pass through a fluid communication hole formed at the other end of the air injection tube and then may enter the dilation balloon, so that the dilation balloon is inflated into a spherical shape.

In accordance with one embodiment of the present invention, the dilation balloon may be constructed such that a portion of a front recess thereof is tightly fitted in an inner side of a tip portion of the other end of the air injection tube so as to form a first tightly-jointed portion, while an end of a rear tilted portion thereof is tightly fitted in a tip end of the support so as to form a second tightly jointed portion.

In accordance with one embodiment of the present invention, the air injection tube may be inserted into and integrated with the external tube serving as a grip to allow easy insertion of the bulged amnion into the uterine cavity using the dilation balloon inflated by the air injection means. The air injection tube 130 may be made of any one selected from a group including latex, latex having a silicon coating thereon, PVC, silicon material and polyurethane material.

In accordance with one embodiment of the present invention, the dilation balloon may be made of any one selected from a group including latex, latex having a silicon coating thereon, PVC, silicon material and polyurethane material. The dilation balloon coming into an inflated state by fluid injected through the air injection tube may become a spherical shape with a front recess.

In accordance with one embodiment of the present invention, a scale mark may be notched or formed at an outer surface of the external tube so as to indicate an insertion depth of the amnion insertion device. A front end of the external tube bends outwardly so as to form a tilted portion, and the tilted portion is coupled, at an outer surface thereof, to a rear portion of the support connected to the dilation balloon. The external tube may be formed to have such a diameter that the air injection tube is inserted thereinto and remains in an immovable state. The external tube may be made of any one selected from a group including FRP (Fiberglass Reinforced Plastic), PVC, a metal material, timber and plastic material.

In accordance with the amnion insertion device 100 of the invention, since the dilation balloon 160 formed at the front end portion of the air injection tube 130 may be stably supported, throughout the rear of the dilation balloon 160, by the support 150, the dilation balloon 160 coming into an inflated state may not be deformed or be pushed backwards when pushing the bulged amnion back into the uterine cavity, to facilitate the cervical cerclage operation. Furthermore, since the external tube 140 and air injection tube 130 are integrated with each other, the amnion insertion device 100 may be entirely gripped by one hand of the operator who in turn operates the amnion device 100 individually, leaving the other hand of the operator free to stitch up the cervix, thereby maximizing efficiency of the cervical cerclage operation.

Additionally, in accordance with the amnion insertion device 100 of the invention, since the dilation balloon 160 has the large thickness and is made of a stretchable material and has the front recess 166 and has a rear side stably supported by the support 150, the operator using the amnion insertion device according to the invention may effectively insert the amnion into the uterine cavity without carrying out the amniocentesis, even when the amnion excessively bulges out of the uterine cavity, by appropriately adjusting a dilation extent of the dilation balloon depending on bulging of the amnion, eliminating the need to discharge some of the amniotic fluid from the amnion in order to reduce the size of the amnion for the the cervical cerclage operation.

BRIEF DESCRIPTION OF THE DRAWINGS

These and/or other aspects of the invention will become apparent and more readily appreciated from the following description of the embodiments, taken in conjunction with the accompanying drawings of which.

DETAILED DESCRIPTION OF THE PREFERRED EMBODIMENTS

Figure 1:
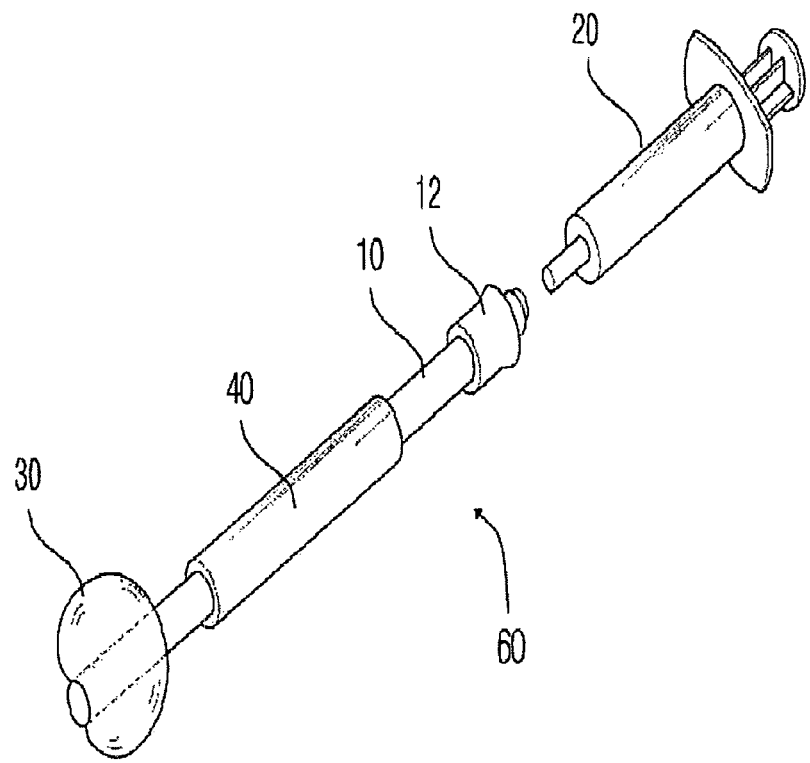
FIG. 1 is a perspective view of a conventional amnion insertion device.
Figure 2:
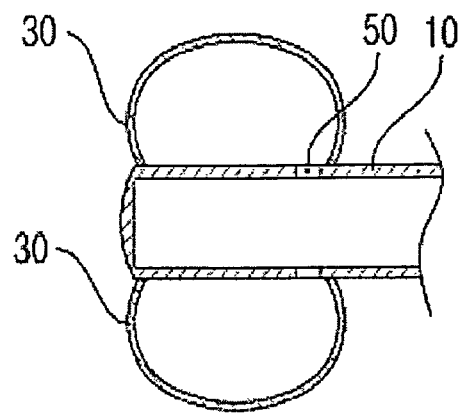
FIG. 2 is a cross-sectional view illustrating a state in which a dilation balloon of the conventional amnion insertion device is inflated.

Reference will now be made in detail to the embodiments of the present invention, examples of which are illustrated in the accompanying drawings, wherein like reference numerals refer to like elements throughout.

Below, an amnion insertion device according to one embodiment of the present invention will be described in detail with reference to the accompanying drawings.

Figure 3:
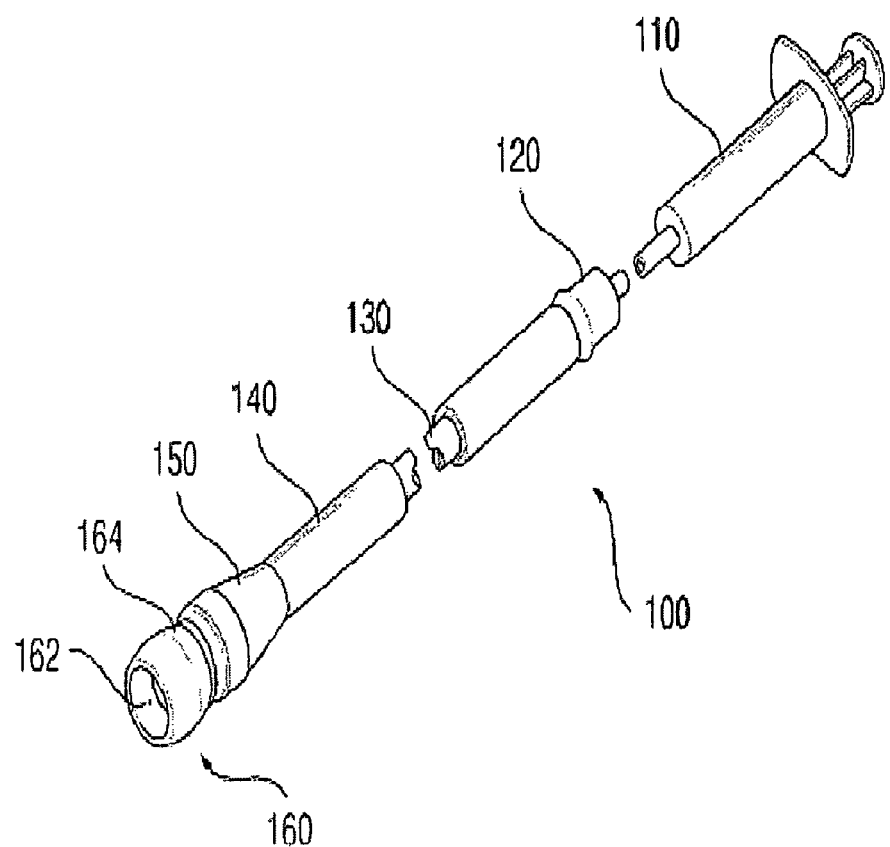
FIG. 3 is a perspective view of an amnion insertion device according to one embodiment of the present invention.

FIG. 3 is a perspective view of an amnion insertion device according to one embodiment of the present invention.

The amnion insertion device according to one embodiment of the present invention may be used in an urgent cervical cerclage operation to treat cervical incompetence in which pregnant woman's cervix effaces and thus her amnion bulges out of the uterine cavity.

Cervical incompetence may be a result of hereditary factors, cervical damage, hormone deficiency, bacterial infection, etc.

Medical treatments for cervical incompetence include a preventive cervical cerclage operation or an urgent cervical cerclage operation carried out when a length of the cervix is observed to be short in an ultrasonic detection.

In the case of cervical incompetence where the cervix effaces and the amnion bulges out of the uterine cavity, the urgent cerclage operation may be executed as the best approach. In the urgent cerclage operation, the bulged amnion is pushed back into a uterine cavity and then the cervix is stitched up, to treat cervical incompetence.

The amnion insertion device according to one embodiment of the present invention used in the cervical cerclage operation may include an air injection tube to inject air through an operation of an air injection means formed at one end of the air injection tube, a dilation balloon formed at the other end of the air injection tube to be inflated by fluid injected through the air injection tube and; an external tube to receive the air injection tube in an integrated manner with the air injection tube at other region than a dilation balloon formation region; and a support coupled between the external tube and dilation balloon.

The dilation balloon is configured such that when the dilation balloon is inflated, the dilation balloon becomes a spherical shape with a front central recess. The front portion is in direct contact with the amnion so as to push the bulged amnion back into the uterine cavity.

The external tube may serve as a grip to allow easy insertion of the amnion into the uterine cavity by preventing the air injection tube fitted in the external tube while being integrated with the external tube from bending when pushing the bulged amnion back into the uterine cavity using the dilation balloon. The external tube may make of a rigid material such as FRP (Fiberglass Reinforced Plastic), PVC, a metal material, timber or plastic material. Among these materials, the plastic material is preferable.

Although not specifically shown in the figures, a scale mark may be notched or formed at an outer surface of the external tube so as to indicate an insertion depth of the amnion insertion device.

Hereinafter, the amnion insertion device according to one embodiment of the present invention will be described in detail with reference to the accompanying drawings.

Figure 4A:
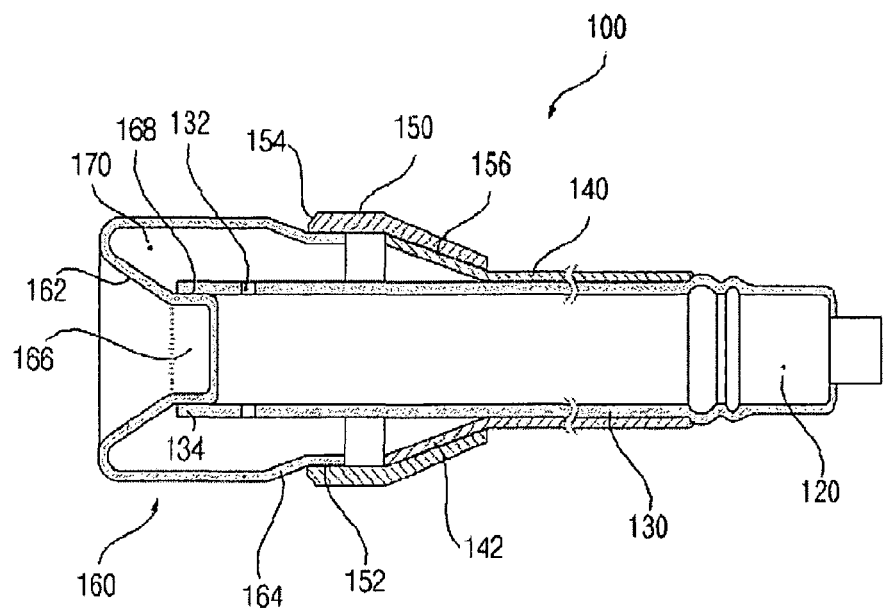
FIG. 4A is a cross-sectional view illustrating a state before a dilation balloon of the amnion insertion device according to one embodiment of the present invention is inflated.
Figure 4B:
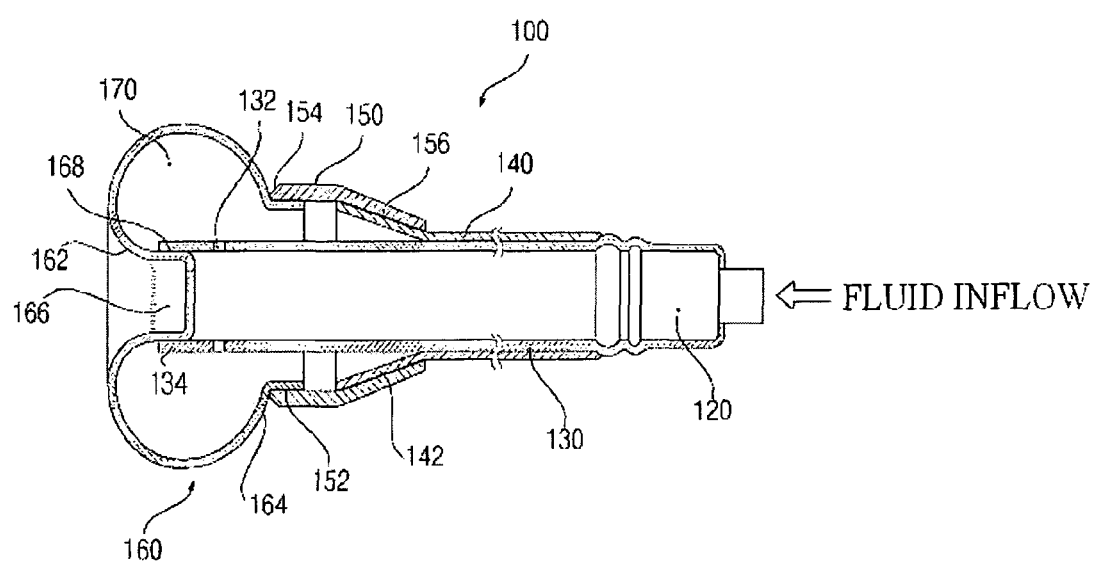
FIG. 4B is a cross-sectional view illustrating a state in which a dilation balloon of the amnion insertion device according to one embodiment of the present invention is inflated.

FIG. 3 is a perspective view of an amnion insertion device according to one embodiment of the present invention. FIG. 4A is a cross-sectional view illustrating a state before a dilation balloon of the amnion insertion device according to one embodiment of the present invention is inflated. FIG. 4B is a cross-sectional view illustrating a state in which a dilation balloon of the amnion insertion device according to one embodiment of the present invention is inflated.

The amnion insertion device 100 according to one embodiment of the present invention used in the cervical cerclage operation, as shown in FIG. 3, may include the air injection tube 130 to inject fluid through an operation of an air injection means 120 formed at a tip of one end of the air injection tube 130, a dilation balloon 160 formed at the other end of the air injection tube 130 to be inflated by fluid injected through the air injection tube 130 so as to directly push the bulged amnion back into the uterine cavity; an external tube 140 to receive the air injection tube 130 in an integrated manner with the air injection tube 130 at other region than a dilation balloon 160 formation region; and a support 150 coupled between the external tube 140 and dilation balloon 160.

The air injection tube 130 has one end connected to the given air injection means 120 which operates so as to inject a predetermined amount of fluid into the air injection tube 130. The predetermined amount of fluid passes through a fluid communication hole 132 formed at the other end of the air injection tube and then is injected into the dilation balloon 160, thereby inflating the dilation balloon 160 so that the dilation balloon 160 has a spherical shape with a front central recess. The dilation balloon 160 is constructed such that a portion of a front central recess thereof is tightly fitted in an inner side of the other end portion 134 so as to form a first tightly-jointed front portion 168, while an end of a rear tilted portion 164 thereof is tightly fitted in a tip end 154 of the support 150 made of a latex, PVC, silicon or polyurethane material so as to form a second tightly-jointed rear portion 152.

The air injection tube 130 is inserted into and integrated with the external tube 140 serving as a grip to allow easy insertion of the bulged amnion into the uterine cavity when pushing the amnion back into the uterine cavity using the inflated dilation balloon. The diameter of the air injection tube 130 is not limited to a particular size. For example, the diameter of the air injection tube 130 may be approximately 4 mm to 8 mm. The air injection tube is preferably made of latex, latex having a silicon coating thereon, PVC, silicon material or polyurethane material.

The air injection means 120 is inserted and coupled to a tip of one end of the air injection tube 130 to inject fluid, for example, air into the air injection tube 130 using an air injector 110 such as a syringe outside of the amnion insertion device and in turn to inflate the dilation balloon 160.

Referring to FIG. 4A, the dilation balloon 160 is formed at an outer region of the other end or front end of the air injection tube 130. The dilation balloon 160 may be made of latex, latex having a silicon coating thereon, PVC, silicon material or polyurethane material. Through the fluid communication hole 132 formed at the other end of the air injection tube 130 so as to communicate with the dilation balloon 160, the predetermined amount of fluid is injected into the a dilation portion 170 of the dilation balloon 160 to inflate the dilation balloon 160.

When the dilation balloon 160 has been inflated by fluid injected through the air injection tube 130, the dilation balloon 160 has a spherical or ellipse shape with a front central recess 166. When the dilation balloon 160 has the spherical or ellipse shape with the front central recess 166, contact area between the dilation balloon 160 and the bulged amnion may be increased, thereby more stably pushing the amnion back into the uterine cavity.

The external tube 140 may serve as a grip to allow easy insertion of the amnion into the uterine cavity by preventing the air injection tube 130 inserted in the external tube 140 from bending when pushing the bulged amnion back into the uterine cavity using the dilation balloon 160 inflated by fluid injected thereto through the air injection tube 130.

The external tube 140 is formed to have such a diameter that the air injection tube 130 is inserted thereinto and remains in an immovable state. As mentioned above, the external tube may be made of a rigid material such as FRP (Fiberglass Reinforced Plastic), PVC, a metal material, timber or plastic material. Among those materials, the plastic material is preferable.

On the other hand, in the conventional amnion insertion device described in the introduction herein, the dilation balloon 30 may move left or right due to a pushing force generated when pushing the bulged amnion back into the uterine cavity using the inflated dilation balloon 160. However, in the amnion insertion device according to one embodiment of the invention, in order to prevent such a movement of the balloon, a rear peripheral portion of the dilation balloon 160 is stably supported by a front portion of the support 500 having a diameter larger than that of the external tube 140. Furthermore, the dilation balloon 160 has a large thickness so as to prevent the dilation balloon 160 from sagging. In this way, in the amnion insertion device according to one embodiment of the invention, it may be possible to more stably push the bulged amnion back into the uterine cavity without damaging the amnion.

The fluid communication hole 132, as shown in FIG. 4A, may be formed nearby a tip end 134 of the air injection tube 130 in which the front central recess 166 of the dilation balloon 160 is tightly fitted. In this way, fluid injected into the air injection tube 130 passes through the fluid communication hole 132 into the dilation balloon 160, thereby inflating the balloon 160.

Operation of the above-mentioned amnion insertion device according to one embodiment of the present invention used in the cervical cerclage operation will be described in detail below.

In the case of cervical incompetence where the cervix effaces due to the hereditary factors, cervical damage, hormone deficiency, bacterial infection, etc. and thus the amnion bulges out of the uterine cavity, the best way to deal with this problem is to carry out the cervical cerclage operation by directly pushing the bulged amnion back into the uterine cavity and then stitching up the cervix; or by discharging some of amniotic fluid from the amnion so as to reduce the size of the amnion (amniocentesis) and then pushing the bulged amnion back into the uterine cavity and stitching up the cervix.

When carrying out such a cervical cerclage operation, the above-mentioned amnion insertion device according to one embodiment of the present invention may be used to insert the bulged amnion back into the uterine cavity. This amnion insertion device operates as follows.

First, when air is injected through the air injection means 120 into the air injection tube 130 using the air injector 110 such as a syringe, the injected air passes through the fluid communication hole 132, as shown in FIG. 4A, formed nearby the tip end 134 of the air injection tube 130 and into the dilation portion 170 of the dilation balloon 160. As a result, the dilation balloon 160 according to one embodiment of the invention is gradually inflated to form a spherical shape in such a manner that a front portion thereof is not substantially transformed with leaving the recess 166 as it is, while the dilation balloon 160 is gradually inflated outwardly at a rear portion thereof.

When the operator pushes the support 150 forwards in a state in which the bulged amnion is in direct contact with a front tilted portion 162 of the dilation balloon 160 inflated into a spherical shape with a front recess 166, the bulged amnion may be stably inserted back into the uterine cavity without damaging the amnion by dilation force of the dilation balloon 160. It is because the dilation balloon 160 surrounds a front end portion of the air injection tube 130 formed in the support 150 in an integrated manner with the support 150, and the rear portion of the balloon 160 is stably supported by the support 150 so as not to be pushed backwards during pushing the support 150 forward. In the above-mentioned amnion insertion device 100 according to embodiment of the invention, the air injection tube 130 to inflate the dilation balloon 160, the support 150 to stably support the dilation balloon 160 at a rear side of the dilation balloon 160, and the external tube 150 surrounding the support 150 are interconnected in an integrated manner. Thus, all operations of the above-mentioned amnion insertion device 100 according to embodiment of the invention may be carried out by a single hand of the operator.

Conventionally, in a case when the amnion excessively bulges out of the uterine cavity and hence the amnion may be damaged if the amnion is forcibly pushed back, in order to prevent such damage of the amnion, amniocentesis should be carried out in advance to discharge some of the amniotic fluid from the amnion and reduce the size of the amnion. After the amniocentesis, the bulged amnion may be pushed back into the uterine cavity using the amnion insertion device. However, in accordance with the invention, since the dilation balloon 160 has the large thickness and has the front recess and has a rear side stably supported by the support 150, the dilation balloon 160 may not move left or right or be pushed backwards when pushing the amnion back into the uterine cavity. Accordingly, even when the amnion excessively bulges out of the uterine cavity, using the amnion insertion device according to the invention, the operator may effectively insert the amnion into the uterine cavity by appropriately adjusting a dilation extent of the dilation balloon in accordance with bulging of the amnion, eliminating the need to perform amniocentesis to discharge some of the amniotic fluid from the amnion so as to reduce the size of the amnion.

After the amnion is completely inserted into the uterine cavity, the operator may stitch up the cervix using the other hand than the hand gripping the amnion insertion device. Hence, it may be possible for the operator to carry out the cervical cerclage operation very effectively.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. An amnion insertion device, comprising:
    an inner tube including
        a distal portion, a proximal portion, and at least one hole disposed on a surface of the distal portion for fluid communication;
    an external tube including
        a tilted distal portion formed in a funnel shape and a flat proximal portion;
    a balloon including
        a tilted distal end portion, a tilted proximal portion, a flat portion defined between the tilted distal and proximal portions, a central portion defined between the tilted distal portions, and the central portion being attached to the inside an end of the distal portion of the inner tube such that the central portion is attached to the inner tube in a recessed form;
    a ring-shaped connector including a top portion,
        the connector being configured to be disposed and surrounded on the surface of the distal portion of the inner tube,
        wherein an end of the tilted proximal portion of the balloon is attached to a top front end of the ring-shaped connector such that the distal portion of the balloon keeps a predetermined distance from the surface of the inner tube, and wherein the tilted distal portion of the external tube is attached to a top rear end of the ring-shaped connector while the flat proximal portion of the external tube overlays on the surface of the inner tube; and
    a balloon support including
        a flat distal portion, a tilted proximal portion formed in a funnel shape, and middle portion defined between the flat distal portion and the tilted proximal portion, the middle portion of the balloon support being disposed on the top portion of the ring-shaped connector such that the flat distal portion securely overlays the tilted proximal portion of the balloon while the tilted proximal portion of the balloon support securely overlays the tilted distal portion of the external tube, the flat distal portion when in an inflated state being adapted to stabilize the balloon at said predetermined distance from the surface of the inner tube, the tilted distal portion and the flat portion when in an inflated state configured for being pressured by both the recessed central portion and the flat distal portion of the ring-shaped connector.

2. The amnion insertion device according to claim 1, further comprising an air injection connector wherein the air injection connector is inserted into said a proximal portion of the inner tube.

3. The amnion insertion device according to claim 1, further comprising an air injector wherein the air injection is inserted into the air injection connector.

4. The amnion insertion device according to claim 1, wherein the balloon is made of latex, latex having a silicon coating thereon, PVC, silicon material or polyurethane material.

5. The amnion insertion device according to claim 1, wherein said external tube is made of rigid material such as FRP, PVC, a metal material, timber or plastic material.

6. The amnion insertion device according to claim 1, wherein the balloon support is made of a latex, PVC, silicon, or polyurethane material.

* * * * *